United States Patent [19]
Adair

[11] Patent Number: 5,290,284
[45] Date of Patent: Mar. 1, 1994

[54] LAPAROSCOPIC SURGICAL LIGATION AND ELECTROSURGICAL COAGULATION AND CUTTING DEVICE

[76] Inventor: Edwin L. Adair, 317 Paragon Way, Castle Pines Village, Colo. 80104

[21] Appl. No.: 20,161

[22] Filed: Feb. 19, 1993

Related U.S. Application Data

[63] Continuation of Ser. No. 877,076, May 1, 1992, abandoned

[51] Int. Cl.⁵ ............................................. A61B 17/39
[52] U.S. Cl. ........................................ 606/37; 606/46; 606/50; 606/139; 606/148
[58] Field of Search ................. 606/139, 144, 148, 37, 606/39, 40, 41, 43–50, 110–113; 128/4

[56] References Cited

U.S. PATENT DOCUMENTS

| | | | |
|---|---|---|---|
| 749,689 | 1/1904 | Houghton | 606/37 |
| 1,932,258 | 10/1933 | Wappler | 606/49 |
| 3,476,114 | 11/1969 | Shannon et al. | |
| 3,877,434 | 4/1975 | Ferguson et al. | |
| 4,018,229 | 4/1977 | Komiya | |
| 4,474,174 | 10/1984 | Petruzzi | 606/46 |
| 4,487,489 | 12/1984 | Takamatsu | |
| 4,602,635 | 7/1986 | Mulhollan et al. | |
| 4,607,621 | 8/1986 | Wheeler | |
| 4,748,982 | 6/1988 | Horzewski et al. | 606/192 |
| 4,935,027 | 6/1990 | Yoon | 606/148 |
| 4,944,727 | 7/1990 | McCoy | 128/4 |
| 4,947,827 | 8/1990 | Opie | 128/4 |
| 5,025,778 | 6/1991 | Silverstein et al. | 128/4 |
| 5,037,433 | 8/1991 | Wilk et al. | 606/222 |
| 5,071,419 | 12/1991 | Rydell et al. | 606/48 |
| 5,084,015 | 1/1992 | Moriuchi | 606/191 |
| 5,085,657 | 2/1992 | Ben-Simhon | 606/45 |
| 5,090,960 | 2/1992 | Michael | 606/191 |
| 5,122,138 | 6/1992 | Manwaring | 606/46 |
| 5,195,958 | 3/1993 | Phillips | 606/40 |
| 5,197,963 | 3/1993 | Parins | 606/41 |
| 5,201,740 | 4/1993 | Nakao et al. | 606/40 |

FOREIGN PATENT DOCUMENTS

| | | | |
|---|---|---|---|
| 2804070 | 8/1979 | Fed. Rep. of Germany | |
| 2265344 | 10/1975 | France | 606/45 |
| 552077 | 11/1982 | U.S.S.R. | |
| 0975006 | 11/1982 | U.S.S.R. | 606/139 |

Primary Examiner—Stephen C. Pellegrino
Assistant Examiner—Jeffrey A. Schmidt
Attorney, Agent, or Firm—Fields, Lewis, Pittenger & Rost

[57] ABSTRACT

A laparoscopic surgical ligation and electrosurgical coagulation device has an elongated handle sized to be received in a trochar and having a central passageway extending therethrough. A first channel is provided in the handle along one side of the passageway and is generally parallel thereto. A second channel is provided in the handle which is generally parallel to the passageway and spaced from the first channel. A suture extends through the central channel passageway and has a loop with a slip knot on the distal end thereof and a pull on the proximal end thereof, so that by pulling on the pull the loop can be drawn tightly about a tissue to be ligated. An electrosurgical wire is slidably received in the first channel and has an electrically insulated body extending through the first channel with an exposed wire hook formed at the distal end thereof for grasping the tissue to pull it through the suture loop. An electrical connector is attached to the proximal end thereof for connection to a source of electrosurgical power. A ligation assist device is slidably received in the second channel which may be in the form of a hypodermic needle for providing anesthesia to the tissue to be ligated or in the form of an optical fiber for carrying laser energy for fulgurating the ligated tissue.

12 Claims, 3 Drawing Sheets

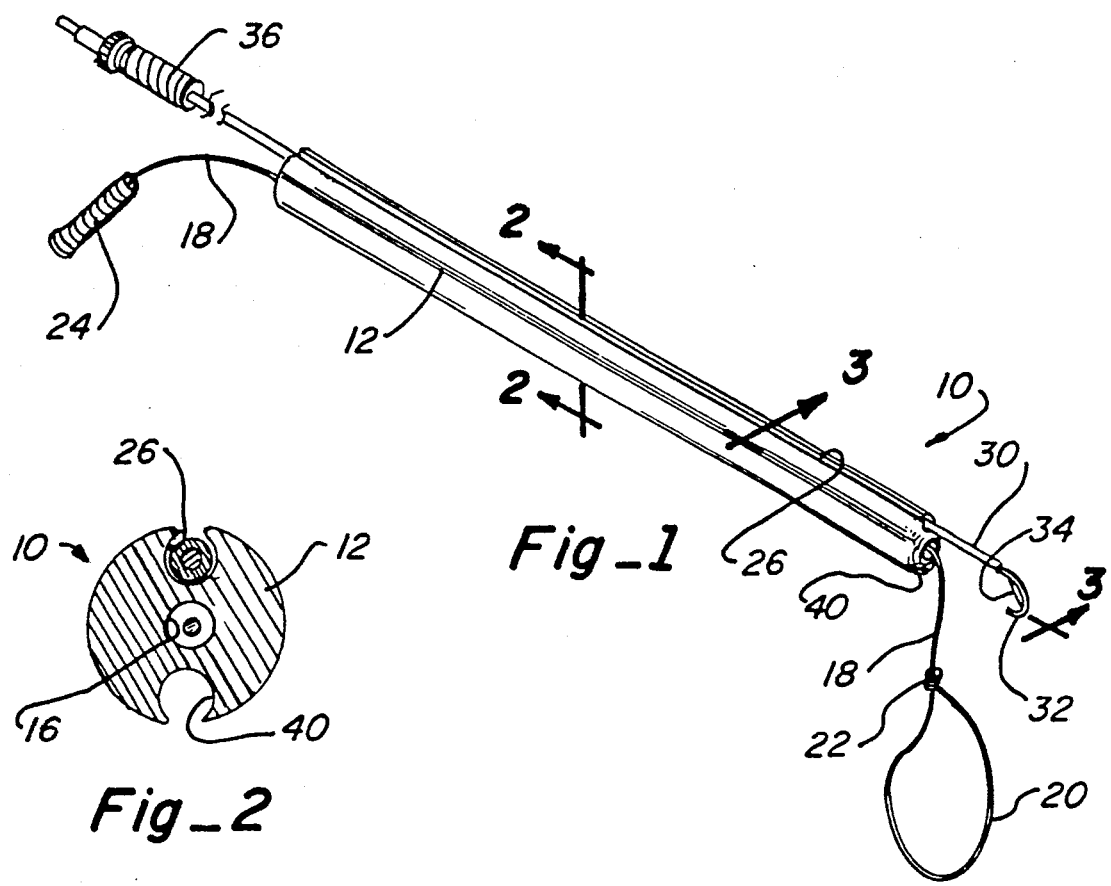
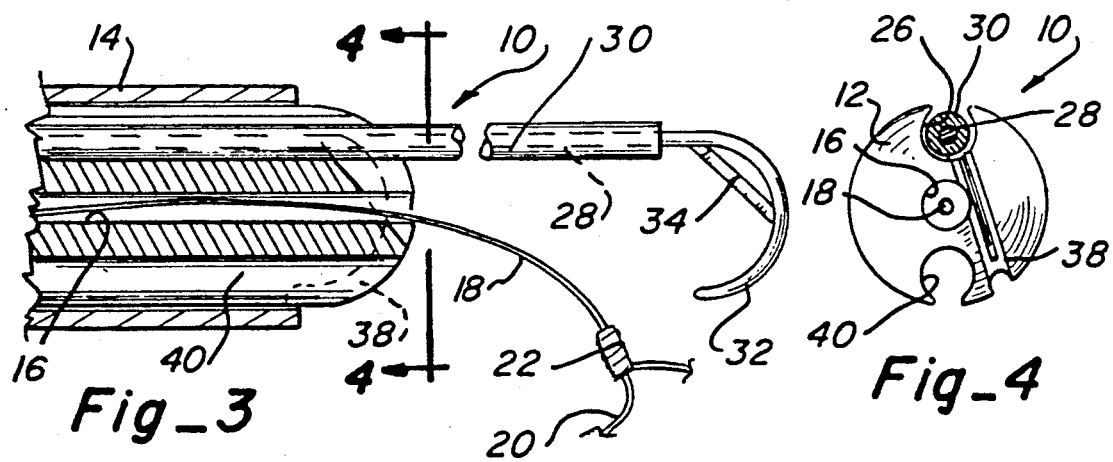
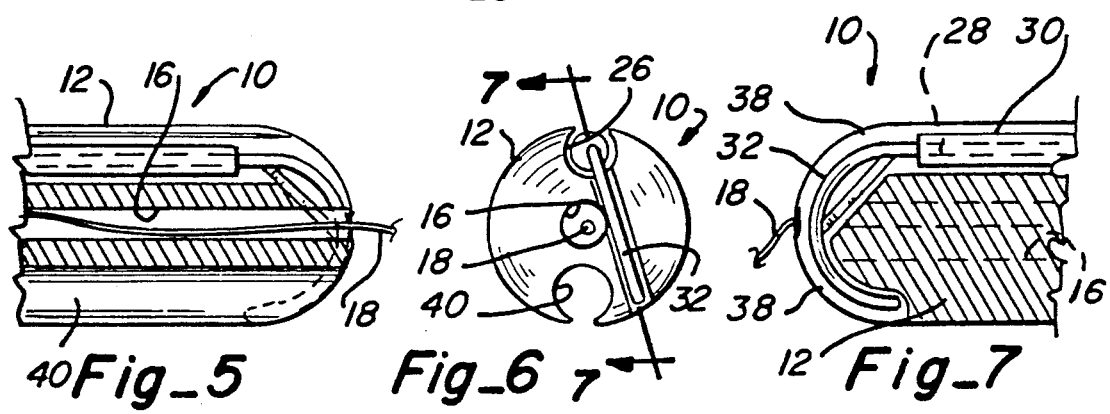

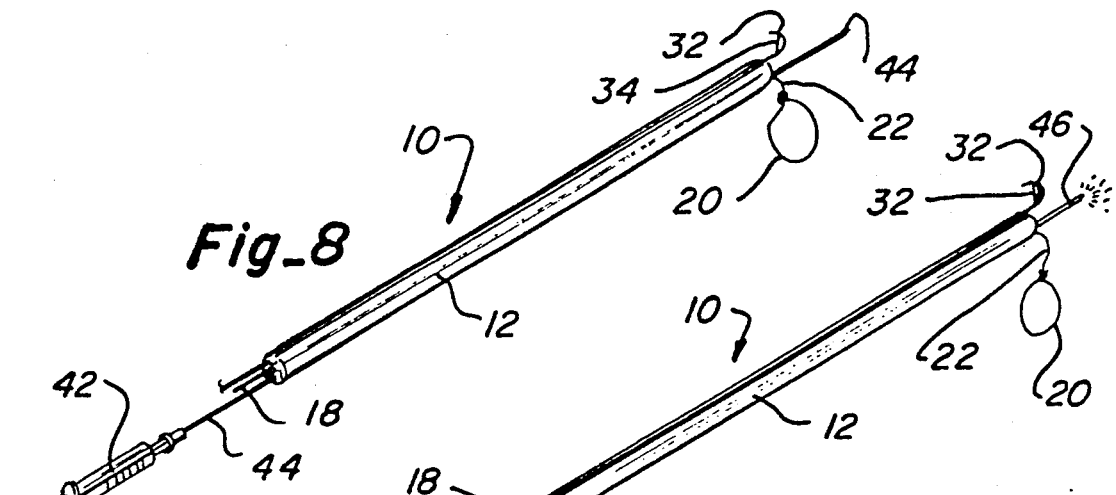
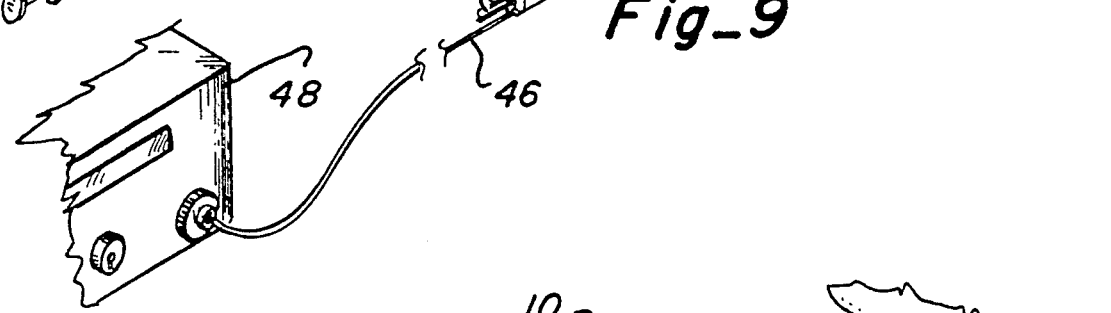
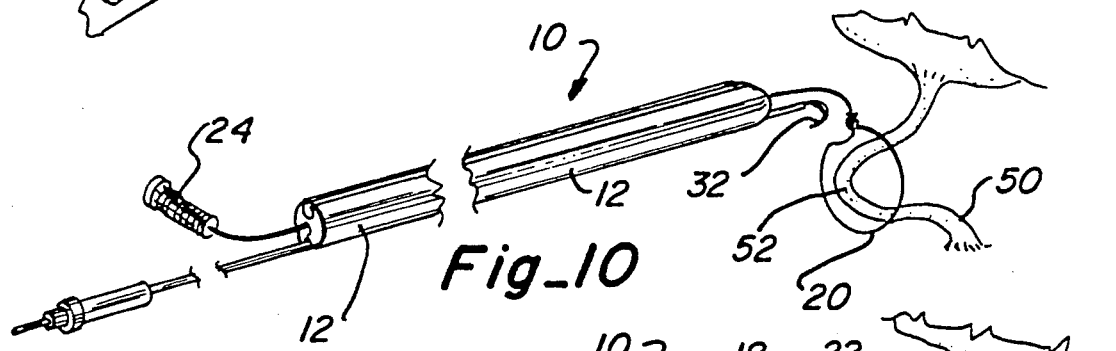
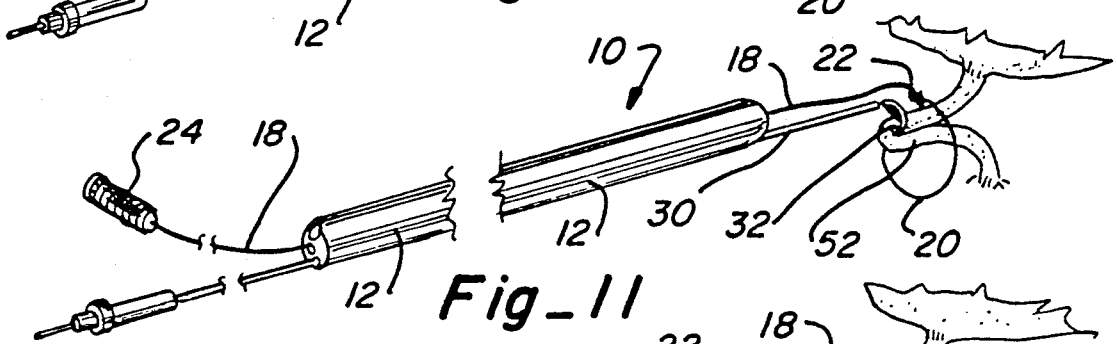
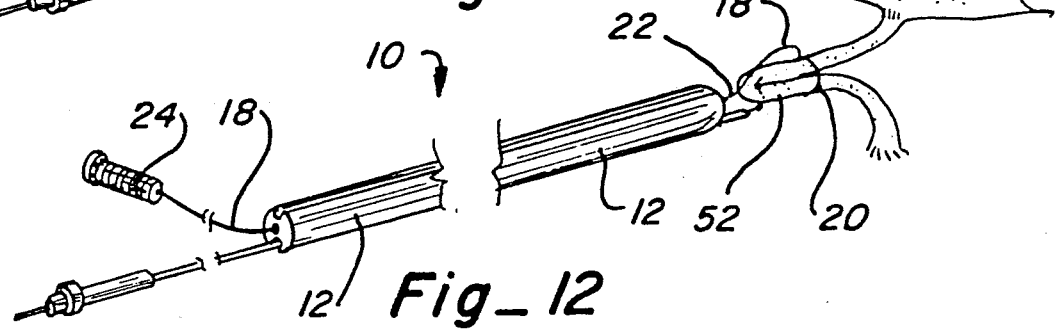

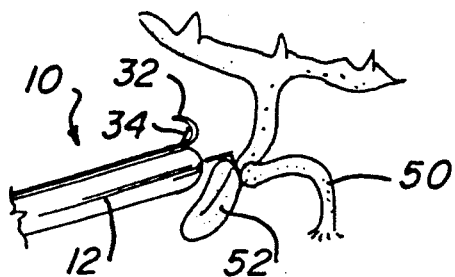
Fig_13
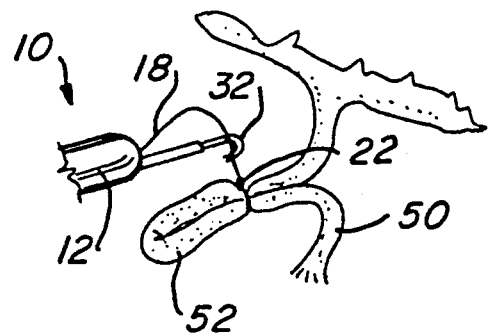
Fig_14
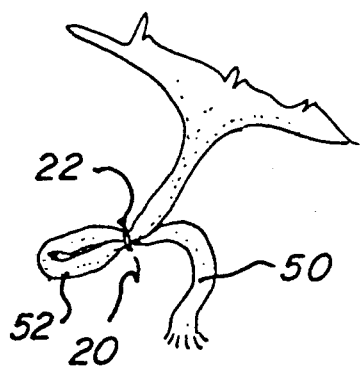
Fig_15
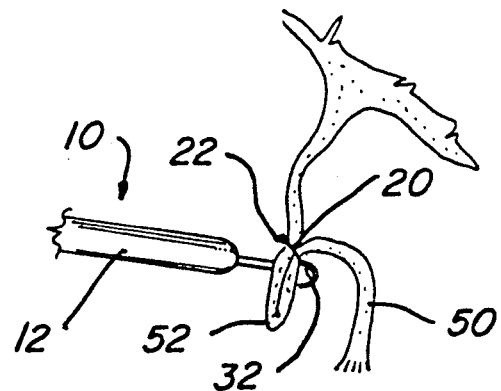
Fig_16
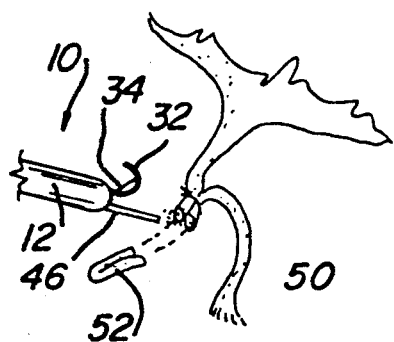
Fig_17

LAPAROSCOPIC SURGICAL LIGATION AND ELECTROSURGICAL COAGULATION AND CUTTING DEVICE

This is a continuation of U.S. application Ser. No. 07/877,076 filed May 1, 1992, now abandoned.

TECHNICAL FIELD

This invention relates to a laparoscopic surgical ligation device and particularly one which provides means for positioning the tissue to be ligated, completing the ligation and for coagulation and fulguration of the ligated tissue.

BACKGROUND ART

There are several manufacturers of laparoscopical surgical devices for tubal ligation. These devices generally utilize a hollow plastic tube containing a preformed loop of suture material with a slip knot at the terminal end. The other end of the suture terminates in a plastic handle or puller which allows easy application of traction to the device to close the loop around the tissue to be ligated inside the patient's body. A tapered distal end on the plastic tube forces the closure of the slip knot as the surgeon applies pressure to the puller causing strangulation of the tissue within the loop. Once the strangulation is sufficient to satisfy the surgeon utilizing the device, scissors are inserted through another trochar and excess suture material is cut-off adjacent the slip knot.

These devices have proven particularly helpful in endoscopically ligating blood vessels, appendix stumps and similar structures. Suture material used in the devices includes both absorbable suture material such as cat gut and non-absorbable suture materials such as silk. Other proprietary types of suture material have also been used.

The disadvantages of these devices is that at least two additional portals, formed with trochars, are required. One is for viewing via a laparoscope and the third portal is for a surgical clamp and/or surgical scissors. The laparoscope is used to visually monitor the procedure being done. A surgical clamp is used to grasp the tissue to be ligated by the suture loop and the scissors are used to cut away excess suture material after the ligation has been completed.

The following patents are exemplary of the prior art:

Komiya, U.S. Pat. No. 4,018,229, shows a rather complex tool for internally attaching a loop and securing it around an affected part in a coeloma.

Shannon et al. U.S. Pat. No. 3,476,114; Mulhollan et al., U.S. Pat. No. 4,602,635, and Ferguson et al., U.S. Pat. No. 3,877,434, each show ligating instruments used to tie a knot to secure the structure being held.

West German Patent No. 2,804,070 and USSR Patent No. 552,077 also show ligature knot tying devices.

Takamatsu, U.S. Pat. No. 4,487,489, shows an endoscope having an electrode loop for clamping a tissue. The endoscope also includes means for viewing the operative site.

Wheeler, U.S. Pat. No. 4,607,621, discloses an endoscopic device utilizing a loop for extending around a body tissue and has an electrode plate upon which the patient rests during the operative procedure for completing an electrical path. The endoscope also has viewing means.

Thus, while the foregoing patents are suitable for their intended purpose, they do not overcome the disadvantages set forth above.

DISCLOSURE OF THE INVENTION

In accordance with this invention, a laparoscopic surgical ligation and electrosurgical coagulation device is provided. This device has an elongated handle sized to be received in a trochar and having a central passageway extending therethrough. A first channel is provided in the handle along one side of the passageway and is generally parallel thereto. A second channel is provided in the handle which is generally parallel to the passageway and spaced from the first channel. A suture extends through the central channel passageway and has a loop with a slip knot on the distal end thereof and a pull on the proximal end thereof, so that by pulling on the pull the loop can be drawn tightly about a tissue to be ligated. An electrosurgical wire is slidably received in the first channel and has an electrically insulated body extending through the first channel with an exposed wire hook formed at the distal end thereof for grasping the tissue to pull it through the suture loop. An electrical connector is attached to the proximal end thereof for connection to a source of electrosurgical power. A agation assist device is slidably received in the second channel which may be in the form of a hypodermic needle for providing anesthesia to the tissue to be ligated or in the form of an optical fiber for carrying laser energy for fulgurating the ligated tissue.

As will be apparent, the device just described is very versatile. The hook, which extends through the first channel, provides means for manipulating the tissue to be ligated and positioning it within the suture loop, so that the loop can be drawn tightly about the tissue to strangulate it. In addition, a cutting blade can be provided on the hook for cutting the suture close to the knot after the suture has been drawn tight. The hook can be an electrosurgical instrument to be used to coagulate the ligated tissue. Also, the second channel can be used initially by a hypodermic needle so that the tissue to be ligated can be anesthetized prior to agation, if need be. Also, the same channel can be used subsequentially for an optical fiber for providing laser energy to fulgurate the ligated tissue.

By the use of this device, only two portals are necessary for ligation procedures, the one for this device and a second portal for viewing through an endoscope. Thus, the laparoscopic procedure is simplified and accomplished with less trauma and discomfort to the patient.

Additional advantages of this invention will become apparent from the description which follows, taken in conjunction with the accompanying drawings.

BRIEF DESCRIPTION OF THE DRAWINGS

FIG. 1 is a perspective view of the laparoscopic surgical ligation and electrosurgical coagulation and cutting device of this invention;

FIG. 2 is an enlarged vertical section, taken along line 2—2 of FIG. 1, showing the internal structure of the handle;

FIG. 3 is an enlarged fragmentary horizontal section, taken along line 3—3 of FIG. 1, showing further details of the distal end of the handle and showing it positioned within a trochar;

FIG. 4 is an end view of FIG. 3, taken along line 4—4 thereof with the trochar omitted;

FIG. 5 is a longitudinal section, similar to FIG. 3, but showing the hook retracted and the trochar omitted;

FIG. 6 is an end view of FIG. 5, showing the hook in retracted position;

FIG. 7 is a section taken along line 7—7 of FIG. 6, showing the recess for receiving the hook;

FIG. 8 is a perspective view of the device showing its use with a hypodermic needle;

FIG. 9 is a perspective view of the device showing its use with a optical fiber for transmitting laser light;

FIG. 10 is a fragmentary perspective view showing the positioning of the suture loop over tissue, such as a tubular portion to be ligated;

FIG. 11 is a fragmentary perspective view, similar to FIG. 10, but showing the hook pulling the tubular tissue to be ligated through the suture loop;

FIG. 12 is a fragmentary perspective, similar to FIGS. 10 and 11, showing the suture loop being drawn around the tubular portion to ligated;

FIG. 13 is a fragmentary perspective view showing the suture loop drawn tight about the tubular portion to be ligated;

FIG. 14 is a fragmentary perspective view showing the knife on the hook being used to cut the suture material adjacent the slip knot;

FIG. 15 is a perspective view of the completed ligation;

FIG. 16 is a fragmentary perspective view showing the hook used as an electrosurgical device for cauterizing and cutting the ligated tissue; and FIG. 17 is a fragmentary perspective view of an optical fiber supplying laser light to fulgurate the ligated tissue.

BEST MODE FOR CARRYING OUT THE INVENTION

In accordance with this invention, a laparoscopic surgical agation and electrosurgical coagulation device 10 is provided. This device is designed primarily for female sterilization in an out patient and/or office setting under local anesthesia. However, it can also be used for ligating blood vessels, for laparoscopic appendectomies or for any other tissue ligation procedure. This device can be introduced through the abdomen to the operative site by means of a 3 mm or 5 mm trochar opening. Viewing is done through an endoscope such as the electronic endoscope shown in my U.S. patent application Ser. No. 769,120, filed Sep. 30, 1991, entitled "Heat Sterilizable Electronic Video Endoscope", which is introduced through a separate trochar. Since this optical catheter is a micro-endoscope, it can also be introduced through a 3 mm opening under local anesthesia. This, however, does not preclude the use of a much larger laparoscope, still utilizing local anesthesia.

Laparoscopic device 10 comprises an elongated body or handle 12, which may be extruded from a medically compatible plastic or other suitable material. The device can be introduced through a trochar of an endoscope, such as trochar 14, shown in FIG. 3. A suitable device is shown in my U.S. Pat. No. 4,869,717, for "Gas Insufflation Needle With Instrument Port".

Handle 10 has a central passageway 16 through which a suture 18 extends. The distal end of suture 18 is formed with a loop 20 by means of a slip knot 22. The slip knot has a diameter larger than that of passageway 16. The proximal end of suture 18 has a pull in a form of a handle 24.

A first channel 26 runs entirely along and intersects the surface of handle 12 to form a longitudinal groove which is generally parallel to passageway 16. This channel slidably receives an electrosurgical wire 28 which is covered by electrical insulation 30 and terminates at the distal end in an exposed wire hook 32. A cutting blade 34 can be provided across the bight of the hook, as best seen in FIG. 3. The proximal end of wire 28 is connected to an electrical connector 36 for attachment to a source of electrosurgical power (not shown). Wire 28 is longitudinally slidable and rotatable within channel 26 so that the tip of hook 32 can be used to grasp the tissue to be ligated and draw it through loop 20, as will be described more fully below. The cutting blade 34 can be used to cut the suture just beyond slip knot 22 after the loop is drawn tight, as further explained below. Conveniently, when not in use, wire 28 can be drawn in the proximal direction so that the hook 32 and blade 34 are received in a recess 38 formed in the distal end of handle 12 as a transverse slot across the convex end of handle 12 and intersecting the end of channel 26, as best seen in FIGS. 3-7.

An optional second channel 40 can be provided which also runs the entire length of handle 12, but spaced from channel 26, such as on the opposite side of passageway 16 from channel 26. This second channel 40 intersects the surface of handle 12 to form a longitudinal groove which is also generally parallel to passageway 16. Channel 40 can be used selectively for receiving other ligation devices. For example, in FIG. 8, a hypodermic syringe 42 is shown with a long needle 44 attached thereto which extends through channel 40. It can be used initially to inject anesthesia to the tissue to be ligated, if this procedure is deemed necessary. Usually, the anesthesia used to deaden the area of the abdomen where the trochars are inserted is sufficient and additional anesthesia is not required.

Alternatively, channel 40 can be used to receive one or more optical fibers, such as optical fiber 46. Conveniently, the optical fiber can be connected to a suitable source 48 of laser light, as shown in FIG. 9, for providing laser light to the operative site to fulgurate the ligated tissue.

The method of preforming a tubal ligation is diagrammatically illustrated in FIGS. 10-17. In FIG. 10, tissue to be ligated, such as fallopian tube 50 is shown. The device 10 is positioned so that suture loop 20 is brought into proximity to a tubal section 52 of the tube 50 which is to be ligated. As previously mentioned, this positioning is viewed through an endoscope inserted through a separate trochar. Once loop 20 is positioned, hook 32 is extended to grasp the tubal section 52 and pull it through suture loop 20 as shown in FIG. 11. The physician then pulls on handle 22 to place suture 18 under traction so that loop 20 begins to pull tight around tubal section 52, as shown in FIG. 12. Thus, slip knot 22 engages the distal end of handle 12 and is held by it as the suture is drawn through knot 22 to draw loop 20 tightly about tubal section 52. Hook 32 then is retracted, as shown in FIG. 13, as the final tightening of the slip knot is completed.

Once suture loop 20 has been pulled tight, the hook 32 can be extended again so that blade 34 can be used to cut suture 18 just above slip knot 22, as shown in FIG. 14. The completed ligation is shown in FIG. 15.

For many physicians, this constitutes the end of the procedure. However, other physicians may choose to use the hook 32 as an electrosurgical device for cauterizing the ligated portion 52. This device may be used as either a monopolar or a bipolar unit. As illustrated in FIG. 16, the wire hook is positioned adjacent ligated tissue 52 and electrosurgical current is supplied to the hook to carry out the cauterizing procedure. If desired, an additional or alternative procedure may be undertaken wherein the laser fiber 46 is used for photo coagulation of ligated section 52 or for photo vaporization of the tissue, as illustrated in FIG. 17. From the foregoing, the advantages of this invention are readily apparent. A laparoscopical surgical ligation and electrosurgical coagulation device has been provided which is simple in construction, yet versatile in use. It can be used for ligating tissue and provides a ready means for cutting the suture once a slip knot has been drawn tight around the tissue to be ligated. The hook has three uses: (1) to position the tissue to be ligated, (2) to use a blade connected thereto for cutting the suture material after ligation and (3) to serve as an electrosurgical device to cauterize the ligated tissue. In addition, the handle has a channel for initially, slidably receiving a hypodermic needle for anesthetizing the tissue to be ligated and subsequently for slidably receiving a laser fiber for coagulation or photo vaporization of the ligated tissue.

This invention has been described in detail with reference to a particular embodiment thereof, but it will be understood that various other modifications can be effected within the spirit and scope of this invention.

I claim:

1. A laparoscopic surgical ligation and electrosurgical coagulation device comprising:
    an elongated handle having a distal end, a proximal end and a central passageway and a first channel extending along said handle on one side of said passageway from said distal end to said proximal end thereof, generally parallel thereto;
    a suture extending through said central passageway and having a loop with a slip knot on the distal end thereof said slip knot having a diameter larger than said central passageway, and a pull on the proximate end thereof so that by pulling on said pull, said slip knot is held by said distal end of said handle so that said loop can be drawn tightly around the tissue to be ligated; and
    an elongated wire slidably received through said first channel and having a hook formed on the distal end for grasping the tissue to be ligated and pulling it through said loop in said suture before the loop is pulled tight.

2. Apparatus, as claimed in claim 1, further comprising:
    a second channel along said handle generally parallel to said central passageway, spaced from said first channel; and
    at least one optical fiber slidably received in said second channel and having a distal end extending beyond the distal end of said handle, for photocoagulation or photo vaporization of the ligated tissue, and having a proximal end connectable to a source of laser light.

3. Apparatus, as claimed in claim 1, further comprising:
    insulation around said wire; and
    means at the proximal end of said wire for connecting it to a source of electrosurgical power so that said hook can be used as an electrosurgical device to cauterize the ligated tissue.

4. Apparatus, as claimed in claim 1, further including:
    a cutting blade located on said hook for cutting said suture after said loop is drawn tight through said slip knot.

5. Apparatus, as claimed in claim 1, further comprising:
    a recess formed in said distal end of said handle in communication with said first channel for receiving said hook in nesting relationship when said hook is not being used.

6. Apparatus, as claimed in claim 1, further comprising:
    a second channel along said handle generally parallel to said central passageway, spaced from said first channel; and
    a hypodermic needle slidably received in said second channel for injecting anesthesia into the tissue to be ligated.

7. A laparoscopic surgical ligation and electrosurgical device comprising:
    an elongated handle having a distal end, a proximal end, a central passageway extending therethrough, a first channel along one side of said passageway and generally parallel thereto and a second channel along said handle, generally parallel to said passageway and spaced from said first channel;
    a suture extending through said central passageway and having a loop with a lip knot on the distal end thereof, said slip knot having a diameter larger than said central passageway, and a pull on the proximal end thereof so that by pulling on the pull, said slip knot is held by said distal end of said handle so that said loop can be drawn tightly about a tissue to be ligated;
    an electrosurgical wire slidably received in said first channel surrounded by an electrically insulated body portion extending through said first channel, said wire having a hook formed at the distal end thereof for grasping the tissue to be ligated and pulling it through said loop in said suture and an electrical connector at the proximal end thereof for connection to a source of electrosurgical power; and
    a ligation assist device slidably received in said second channel.

8. Apparatus, as claimed in claim 7, wherein:
    said ligation assist device is in the form of a hypodermic needle slidably received in said second channel, for injecting anesthesia into the tissue to be ligated.

9. Apparatus, as claimed in claim 7, wherein:
    the ligation assist device is in the form of at least one optical fiber slidably received in said second channel and having a distal end extending beyond the distal end of said handle, for photocoagulation or photo vaporization of the ligated tissue, and having a proximal end connectable to a source of laser light.

10. A method of tubal ligation comprising the steps of:
    introducing a trochar through the abdomen of the patient;
    inflating the abdomen of the patient;
    introducing a laparoscopic surgical ligation and surgical device through the trochar;
    pulling a section of the tube to be ligated though a loop formed by a slip knot in a suture;
    pulling the suture loop tight around the tube section to be ligated;

cutting the suture adjacent the slip knot; and fulgurating the ligated tubal portion with an electrosurgical device.

11. A medical device for supplying a suture and one or more medical instruments to an operative site through a first trochar, the site being viewed by the surgeon through a second trochar, said device comprising:

an elongated cylindrical body having an outer surface, a convex distal end and a proximal end;

a central passageway extending through said cylindrical body from said proximal end to said convex distal end for receiving a suture;

a first channel extending generally parallel to said central passageway along the edge of said cylindrical body from said distal end to said proximal end thereof for slidably receiving a first surgical instrument; and a traverse slot extending across said convex distal end of said body and intersecting said first channel to receive the distal end of the first surgical instrument when it is not in use.

12. A medical device for supplying a suture and one or more medical instruments to an operative site through a first trochar, the site being viewed by the surgeon through a second trochar, said device comprising:

an elongated cylindrical body having an outer surface, a convex distal end and a proximal end;

a central passageway extending through said cylindrical body from said proximal end to said distal end for receiving a suture;

a first channel extending generally parallel to said central passageway along the edge of said cylindrical body from said distal end to said proximal end thereof for slidably receiving a first surgical instrument, said first channel intersecting said surface of said body;

a second channel extending generally parallel to said central passageway along the edge of said cylindrical body from said distal and to said proximal end thereof and located opposite said first channel for slidably receiving a second surgical instrument; and a transverse slot extending across said convex distal end of said body and intersecting said first channel to receive the distal end of the first surgical instrument when it is not in use.

* * * * *

UNITED STATES PATENT AND TRADEMARK OFFICE
CERTIFICATE OF CORRECTION

PATENT NO. : 5,290,284
DATED : March 1, 1994
INVENTOR(S) : Edwin L. Adair

It is certified that error appears in the above-indentified patent and that said Letters Patent is hereby corrected as shown below:

Column 6, line 27, delete "lip" and insert --slip--.

Signed and Sealed this

Thirteenth Day of September, 1994

Attest:

BRUCE LEHMAN

*Attesting Officer*  *Commissioner of Patents and Trademarks*